United States Patent
Ikeda et al.

(10) Patent No.: US 8,975,080 B2
(45) Date of Patent: Mar. 10, 2015

(54) BIOSENSOR CALIBRATION METHOD

(71) Applicant: Tanita Corporation, Itabashi-ku (JP)

(72) Inventors: Satoshi Ikeda, Itabashi-ku (JP); Mariko Kose, Itabashi-ku (JP); Tatsuro Murayama, Itabashi-ku (JP); Yuri Kinoshita, Itabashi-ku (JP)

(73) Assignee: Tanita Corporation, Tokyo (JP)

( * ) Notice: Subject to any disclaimer, the term of this patent is extended or adjusted under 35 U.S.C. 154(b) by 25 days.

(21) Appl. No.: 13/804,937

(22) Filed: Mar. 14, 2013

(65) Prior Publication Data

US 2014/0080167 A1    Mar. 20, 2014

(30) Foreign Application Priority Data

Sep. 14, 2012  (JP) .................................. 2012-203491

(51) Int. Cl.
*G01N 33/00* (2006.01)
*G01N 33/66* (2006.01)
*C12Q 1/26* (2006.01)
*G01N 27/327* (2006.01)

(52) U.S. Cl.
CPC .............. *C12Q 1/26* (2013.01); *G01N 27/3274* (2013.01)
USPC ....... 436/8; 436/14; 436/95; 435/14; 73/1.01; 73/1.02; 702/100

(58) Field of Classification Search
CPC ..... G01N 33/48; G01N 33/66; G01N 27/327; G01N 27/3271; G01N 27/3273; G01N 27/3274; C12Q 1/26
USPC ........ 436/8, 14, 63, 95, 149, 150; 435/14, 25; 73/1.01, 1.02, 1.03; 702/100
See application file for complete search history.

(56) References Cited

U.S. PATENT DOCUMENTS

| 2002/0014409 A1 | 2/2002 | Matsumoto et al. |
| 2008/0154107 A1* | 6/2008 | Jina ................................ 600/347 |
| 2008/0159914 A1* | 7/2008 | Ohashi et al. ................. 422/68.1 |

(Continued)

FOREIGN PATENT DOCUMENTS

| EP | 1936373 A1 | 6/2008 |
| JP | 57-97431 A | 6/1982 |

(Continued)

OTHER PUBLICATIONS

Extended Search Report issued on Dec. 13, 2013 by the European Patent Office, in corresponding European Patent Application No. 13158882.4 (6 pages).

(Continued)

*Primary Examiner* — Maureen Wallenhorst
(74) *Attorney, Agent, or Firm* — Buchanan Ingersoll & Rooney P.C.

(57) ABSTRACT

A biosensor calibration method configured to measure a concentration of a specific substance contained in sample liquid to be measured, including: a first step configured to acquire a first output value that is output by the biosensor when first calibration liquid is brought into contact with the biosensor; a second step configured to acquire a second output value that is output by the biosensor when second calibration liquid having a different concentration from that of the first calibration liquid is continuously brought into contact with the biosensor after the first step and determine time for replacement of the biosensor on the basis of the first output value and the second output value.

13 Claims, 11 Drawing Sheets

(56) References Cited

U.S. PATENT DOCUMENTS

| | | | |
|---|---|---|---|
| 2009/0018426 A1* | 1/2009 | Markle et al. | 600/365 |
| 2009/0099781 A1* | 4/2009 | Miyashita | 702/19 |
| 2011/0198241 A1* | 8/2011 | Murakami | 205/792 |
| 2012/0096918 A1 | 4/2012 | Crane et al. | |
| 2012/0293181 A1* | 11/2012 | Murayama | 324/439 |

FOREIGN PATENT DOCUMENTS

| | | | |
|---|---|---|---|
| JP | 2-159548 A | | 6/1990 |
| JP | 5-164735 A | | 6/1993 |
| JP | 2002-48750 A | | 2/2002 |
| JP | 2004-163349 A | | 6/2004 |
| JP | 2008-175801 | | 7/2008 |
| JP | 2009-270883 | * | 11/2009 |
| WO | 96/22730 A1 | | 8/1996 |
| WO | 2008/141243 A2 | | 11/2008 |

OTHER PUBLICATIONS

Office Action issued on Jun. 20, 2014, by the Japanese Patent Office in corresponding Japanese Patent Application No. 2012-203491. (3 pages).

* cited by examiner (A)

(B)

(C)

(D)

(A)

(B)

(C)

(D)

(E)

BIOSENSOR CALIBRATION METHOD

BACKGROUND OF THE INVENTION

1. Field of the Invention

The present invention relates to a measuring method of a biosensor configured to measure a concentration of a specific substance contained in sample liquid to be measured.

2. Description of the Related Art

A biochemical instrument provided with a biosensor such as a glucose sensor used in the related art which can be used repeatedly needs to be calibrated regularly by using calibration liquid at a constant concentration because sensitivity of the sensor varies due to a variety of factors (for example, the number of times of usage, the duration of usage, etc.). As a calibration method, a method of applying the calibration liquid on the sensor at once (one-point calibration), or a method of calibrating continuously by a plurality of times (several-point calibration) are used and, for example, a calibration method described in JP-A-2008-175801 is also proposed.

However, with the one-point calibration which performs the calibration only once, there is a problem that the sufficient calibration may not necessarily be achieved due to how a user applies the calibration liquid (difference in the momentum and the quantity of the application of the calibration liquid), and hence the accuracy is not stabilized.

The several-point calibration which performs the calibration several times continuously is performed in general by executing a first calibration in the order of dropping of the calibration liquid, cleaning, and waiting, and then repeating a second calibration in the order of dropping of the calibration liquid, cleaning, and waiting (see FIG. 9). However, for the user, a labor or a waiting time in association with performing these operations repeatedly as-is, specifically, a cleaning operation for cleaning the calibration liquid in the first calibration and the waiting time until the second calibration is started are required, so that the user feels inconvenience about such a complicated calibration operation and the working time associated thereto.

SUMMARY

Accordingly, the invention provides a biosensor calibration method capable of reducing a period required for a calibration process and improving the accuracy of a sensor by leaving the biosensor having come into contact with a first calibration liquid without being cleaned, bringing a second calibration liquid having a different concentration from that of a first calibration liquid into contact with the biosensor to perform the calibration of the sensitivity of the biosensor.

DESCRIPTION OF PREFERRED EMBODIMENT

In order to solve the above described problems, there is provided a biosensor calibration method configured to measure a concentration of a specific substance contained in sample liquid to be measured, including: a first step of acquiring a first output value that is output by the biosensor when first calibration liquid is brought into contact with the biosensor; and a second step of acquiring a second output value that is output by the biosensor when second calibration liquid having a different concentration from that of the first calibration liquid is continuously brought into contact with the biosensor after the first step and determining time for replacement of the biosensor on the basis of the first output value and the second output value.

Preferably, the concentration of the second calibration liquid is higher than the concentration of the first calibration liquid.

Preferably, the second calibration liquid has a concentration twice to six times that of the first calibration liquid.

Preferably, a determination of the time for replacement in the second step is a determination of whether or not the first output value and the second output value satisfy the relationship $$(\text{first output value} \times n) \times (1-0.35) \leq \text{second output value} \leq (\text{first output value} \times n) \times (1+0.05)$$

(where, $n$=concentration of the second calibration liquid/concentration of the first calibration liquid).

Preferably, the biosensor calibration method further includes a step of cleaning the biosensor after the second step.

Preferably, the biosensor calibration method further includes a first notifying step of encouraging a user to bring the second calibration liquid into contact with the biosensor from 6 seconds to 20 seconds after the contact of the first calibration liquid.

Preferably, the biosensor calibration method further includes a second notifying step of encouraging the user to clean the biosensor from 6 seconds to 20 seconds after the contact of the second calibration liquid.

Advantages of the Invention

According to the invention, with the calibration method in which the second step of acquiring the sensor output when the second calibration liquid having a different concentration from the first calibration liquid is brought into contact is performed continuously from the first step of acquiring the sensor output when the first calibration liquid is brought into contact with the biosensor, and a cleaning operation for cleaning the first calibration liquid is not performed, so that reduction of the number of the operation steps and the working time required for the user is achieved.

By the employment of calibration liquids having a different concentrations as the first calibration liquid and the second calibration liquid, variations in measurement errors of the measuring sensor by machine type after the calibration may be reduced in comparison with the calibration method on the basis of the one-point calibration of the related art, so that the result of measurement with high precision with small measurement errors by machine type may be obtained in the measurement of the sample liquid to be measured.

BRIEF DESCRIPTION OF THE PREFERRED EMBODIMENT

DESCRIPTION OF PREFERRED EMBODIMENT

Biochemical Instrument

Figure 1:
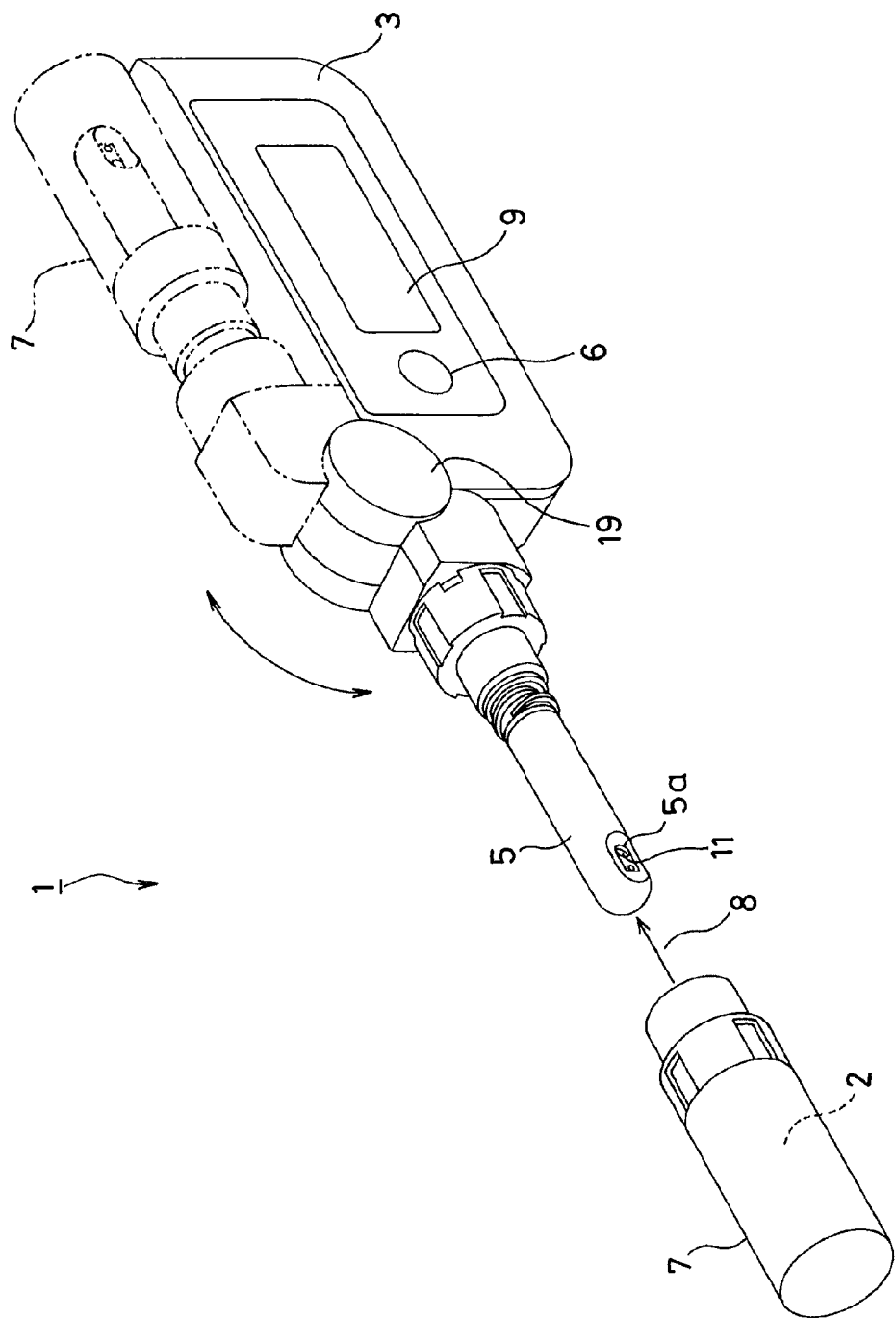
FIG. 1 is a perspective view schematically illustrating an entire configuration of a biochemical instrument according to an embodiment of the invention.

Referring now to the drawings, an embodiment of the biochemical instrument for using a calibration method of the invention will be described. FIG. 1 is a perspective view schematically illustrating a general configuration of a biochemical instrument 1 according to the embodiment of the invention, and FIG. 2 is a block diagram illustrating an electric configuration of the biochemical instrument 1 illustrated in FIG. 1.

Figure 2:
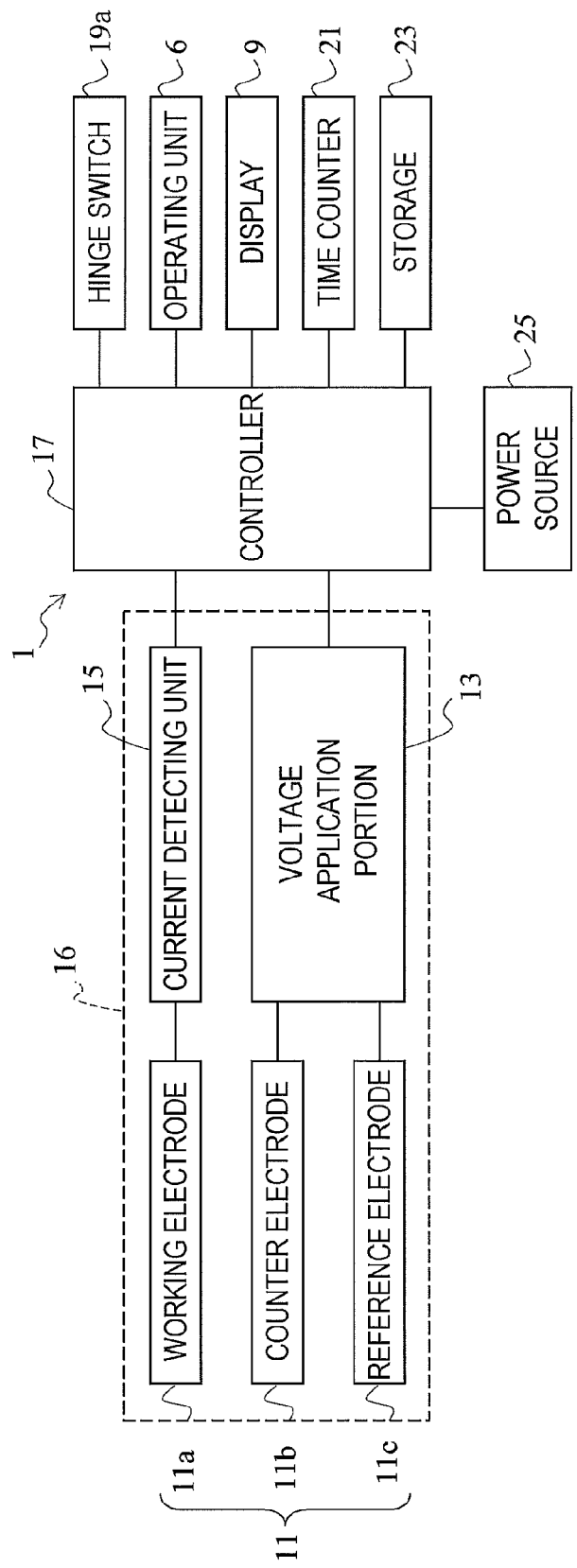
FIG. 2 is a block diagram illustrating an electrical configuration of the biochemical instrument illustrated in FIG. 1.

The biochemical instrument 1 illustrated in FIG. 1 is a configuration of the entire system of the biochemical instrument 1, and FIG. 2 illustrates the electric configuration of the biochemical instrument 1. The invention is not limited to these configurations as long as the biosensor calibration method of the invention may be performed.

As illustrated in FIG. 1 and FIG. 2, the biochemical instrument 1 includes at least a biochemical instrument body 3, a sensor holder 5, an operating unit 6, a hinge 19, and a cap 7.

The biochemical instrument body 3 is a housing having a controller 17 as the electric configuration illustrated in FIG. 2, a time counter 21 and the like integrated therein, and a display (LCD (Liquid Crystal Display)) 9 which corresponds to a display unit (notifying unit) which displays various items of information to users is provided at a substantially center of the biochemical instrument body 3. The display 9 displays measured values, measured data and time, and so on. The operating unit 6 is provided on the biochemical instrument body 3 and is mainly an operating device for performing an operation for displaying measured values in the past on the display 9, an operation for switching the mode to a calibration mode, an operation for turning ON and OFF a power source, and so on.

The sensor holder 5 is replaceably provided on the hinge 19, which is rotatably provided on an upper left shoulder portion of the biochemical instrument body 3 illustrated in FIG. 1.

The sensor holder 5 is formed into an elongated cylindrical shape toward a free end portion and is provided with a glucose sensor (biosensor) 11 in an opening 5a on one side surface in the vicinity of the free end portion so as to allow storage liquid 2 and sample liquid to be measured to come into contact with the glucose sensor 11 from the outside through the opening 5a.

The sensor holder 5 is configured to allow the biochemical instrument 1 to perform measurement in a state in which the sensor holder 5 is expanded (a state illustrated in FIG. 1 by a solid line), and is mounted on the biochemical instrument body 3 via the hinge 19 so as to be rotatable in the directions indicated by an arrow in FIG. 1.

The glucose sensor 11 includes at least a working electrode 11a and a counter electrode 11b as sensor electrodes, and is configured to measure a base current generated by an application of a predetermined potential in a state in which the working electrode 11a and the counter electrode 11b are in contact with the storage liquid 2, and measure a peak current generated by the application of the predetermined potential in a state in which the working electrode 11a and the counter electrode 11b are in contact with (or immersed into) the sample liquid to be measured (or calibration liquid).

The cap 7 is formed into a cylindrical shape as a whole, is used for storing the sensor holder 5 of the biochemical instrument 1, and is configured to fit the sensor holder 5 from a distal end thereof in the direction indicated by an arrow 8 to cover the sensor holder 5. The biochemical instrument 1 is stored in a state in which the sensor holder 5 in an expanded state with the cap 7 mounted thereon is rotated toward the biochemical instrument body 3 (a state illustrated by a double-dashed chain line in FIG. 1) via the hinge 19, and hence the sensor holder 5 is covered with the cap 7 and folded onto the upper surface side of the biochemical instrument body 3. The storage liquid (reference liquid) 2 for returning the base current value of the glucose sensor 11 to a reference value is filled in the interior of the cap 7. The storage liquid 2 in the interior of the cap 7 is a storage solution in which a specific substance has a zero-concentration, and is preferably a solution which is capable of keeping the state of the glucose sensor 11 always in an optimal state. However, any reference liquid is applicable as long as a reference liquid is capable of presenting a reference concentration which may be used as a reference value at the time of measurement of the concentration.

Although the description will be given later, the time counter 21 measures an elapsed time from a contact of the working electrode 11a and the counter electrode 11b with the storage liquid 2 until the base current is measured, and a measuring time from a contact of the glucose sensor 11 with the sample liquid to be measured until the peak current for a certain period (for example, 6 seconds) is measured. The controller 17 acquires a concentration of the sample liquid to be measured on the basis of the base current value of the base current and the peak current value of the peak current acquired by the glucose sensor 11.

The electric configuration of the biochemical instrument 1 is integrated in the biochemical instrument body 3. Subsequently, detailed configuration will be described with reference to FIG. 2.

The electric configuration integrated in the biochemical instrument body 3 includes the controller 17 composed of a microcomputer, a potentiostat 16, a hinge switch 19a, the operating unit 6, the display 9, the time counter 21, a storage 23, and a power source 25, and the respective components are electrically connected respectively to the controller 17.

The potentiostat 16 is a measuring unit, includes the glucose sensor 11 of a three-electrode system in which the working electrode 11a, the counter electrode 11b, and a reference electrode 11c are arranged on an insulating substrate, a current detecting unit 15 configured to detect an electric current of the working electrode 11a, and a voltage application portion 13 configured to apply voltages respectively on the counter electrode 11b and the reference electrode 11c, and is connected to the controller 17.

The working electrode 11a of the glucose sensor 11 is covered with an enzyme film of glucose oxidase, and has a configuration in which the potentiostat 16 as the measuring unit controls the potential of the counter electrode 11b so as to maintain the potential between the working electrode 11a and the reference electrode 11c always in constant by the signal from the controller 17 to detect the current value of the current flowing from the working electrode 11a to the counter electrode 11b. Although the glucose sensor of a three-electrode system is used in this embodiment, a glucose sensor of a two-electrode system which does not have the reference electrode 11c (third electrode) may also be used.

The storage 23 includes, for example, an RAM (Random Access Memory) or an ROM (Read Only Memory), and includes a program which operates the biochemical instrument 1, data detected by the glucose sensor 11, the number of times of usage, the data and time of previous calibration, the state of occurrence of errors of the biochemical instrument 1 (the glucose sensor 11) stored therein.

Switching of the biochemical instrument 1 of this embodiment between a measurable state and a waiting state is performed by the hinge switch (hinge portion) 19 integrated into the hinge 19. When the sensor holder 5 is brought into a state in which the sensor holder 5 is expanded with respect to the biochemical instrument body 3 (the state illustrated by the solid line in FIG. 1, a first state), the instrument is brought into the measurable state in which a step of measuring the concentration of a specific substance contained in the sample liquid to be measured may be performed, and when the cap 7 is mounted and the sensor holder 5 is brought into a state of being folded (a second state, the state illustrated by the double-dashed chain line in FIG. 1), the measurable state is released, and the biochemical instrument 1 is brought into the waiting state. In the waiting state, it is preferable to configure the glucose sensor 11 immersed in the storage liquid 2 in the cap 7 to be applied with a predetermined potential by an instruction from the controller 17. In this configuration, the state of the biochemical instrument 1 may be switched from the second state to the first state without waiting for a period from the initiation of the application of the predetermined potential until the stabilization of the base current, so that the instrument may be used immediately after the cap 7 has removed from the sensor holder 5, whereby the convenience for the user is improved.

The time counter 21 as a time counter which counts the time is used for counting the time from when the glucose sensor 11 is immersed in the storage liquid 2 in the cap 7 until the peak current of the sample liquid to be measured is detected by the current detecting unit 15. When the sensor holder 5 is folded into the second state, the biochemical instrument 1 is brought into the waiting state by the hinge switch 19, and the count of the elapsed time by the time counter 21 is started. Also, the time counter 21 measures the measuring time from the contact of the glucose sensor 11 with the sample liquid to be measured until the peak current for the certain period.

This embodiment is configured to count the elapsed time and perform the measuring step under the condition that the timing when the glucose sensor 11 is immersed in the storage liquid 2 and the timing when the hinge 19 is folded are performed in the same timing. In other words, the elapsed time from when the glucose sensor 11 is immersed in the storage liquid 2 until the sensor holder 5 is expanded and the peak current value of the sample liquid to be measured is measured with the current detecting unit 15 is acquired by counting a period from when the sensor holder 5 is folded (that is, from when the second state is achieved) until the sensor holder 5 is expanded and the peak current of the sample liquid to be measured is measured by the current detecting unit 15.

The biochemical instrument 1 of this embodiment has a configuration to switch the state of the biochemical instrument 1 between the measurable state and the waiting state by rotating the sensor holder 5 via the hinge 19. However, the state of the biochemical instrument 1 may be switched by inserting and pulling out a stand having the storage liquid 2 of the cap 7. A configuration to switch the state of the biochemical instrument 1 by the operation of the operating unit 6 and a configuration in which a liquid crystal having a touch panel function is used for the display 9 and the switching is achieved by the operation thereof are both applicable.

The glucose sensor 11 is subject to chemical reaction in the sample liquid to be measured or the calibration liquid as follows. By the action of the glucose oxidase, glucose in the sample liquid to be measured (or the calibration liquid) is oxidized, and oxygen is reduced to hydrogen peroxide, so that gluconolactone and hydrogen peroxide are generated. At this time, by an application of a voltage to the electrodes (the working electrode 11a and the counter electrode 11b) from the voltage application portion 13, oxidizing reaction of the hydrogen peroxide is generated on the working electrode 11a, thereby generating electrons and an oxidation current flows from the working electrode 11a to the counter electrode 11b, and the flowed oxidation current is measured as an oxidation current value. Since the amount of generation of the hydrogen peroxide is proportional to the amount of glucose, the concentration of glucose can be measured by measuring the oxidation current value of the hydrogen peroxide. In other words, when measuring the sample liquid to be measured using the biochemical instrument 1, the glucose concentration in the sample liquid to be measured is measured on the basis of a difference between a base current value of a base current flowed by an application of a constant potential to a point between both electrodes (the working electrode 11a and the counter electrode 11b) in a state of being immersed in storage liquid which does not contain the glucose and a peak current value of an oxidation current flowing between the both electrodes by the application of a constant potential to a point between the both electrode (the working electrode 11a and the counter electrode 11b) in the sample liquid to be measured.

Flow of Measuring Method

Figure 3A:
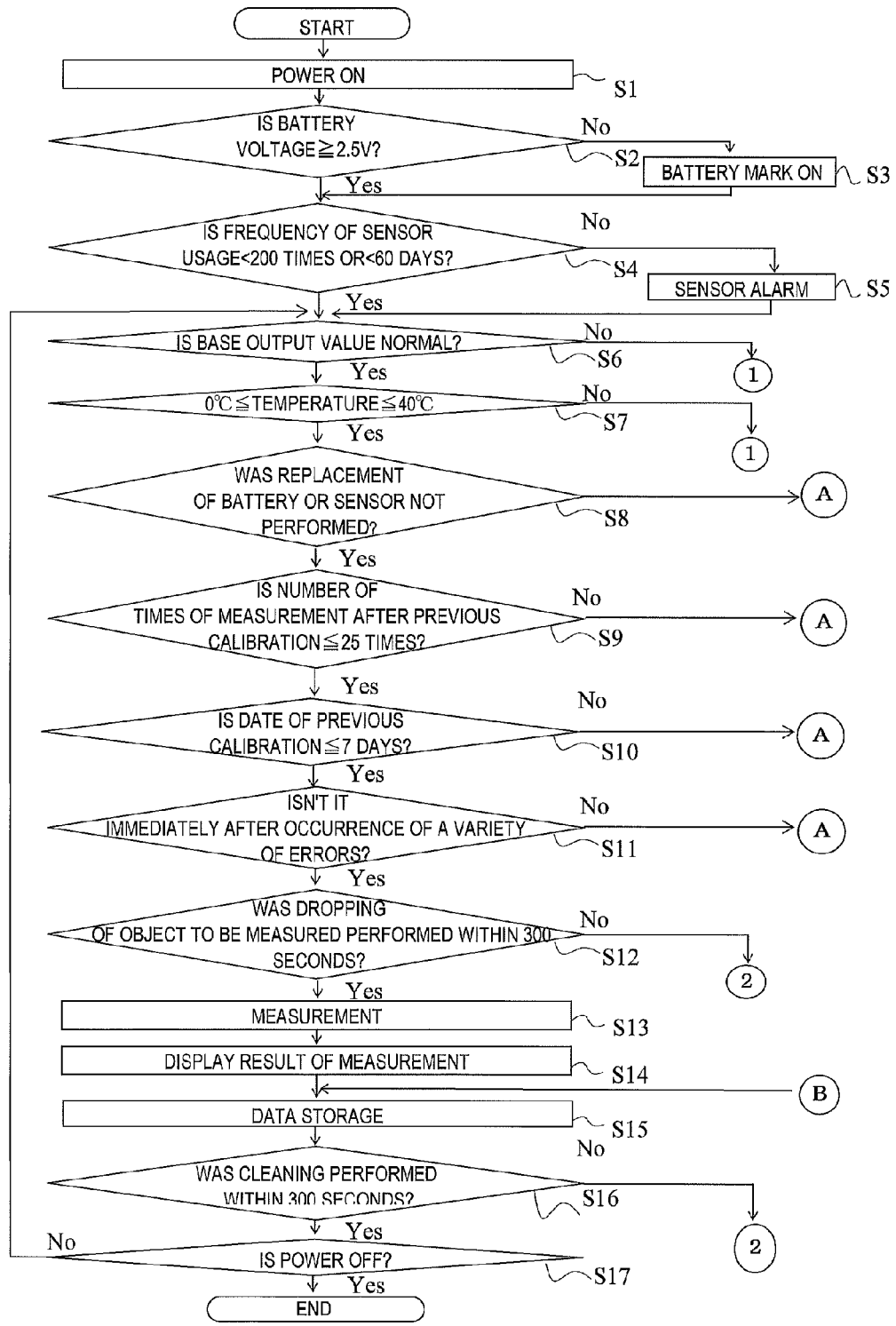
FIG. 3A is a flowchart illustrating a measuring method using the biochemical instrument illustrated in FIG. 1.
Figure 3B:
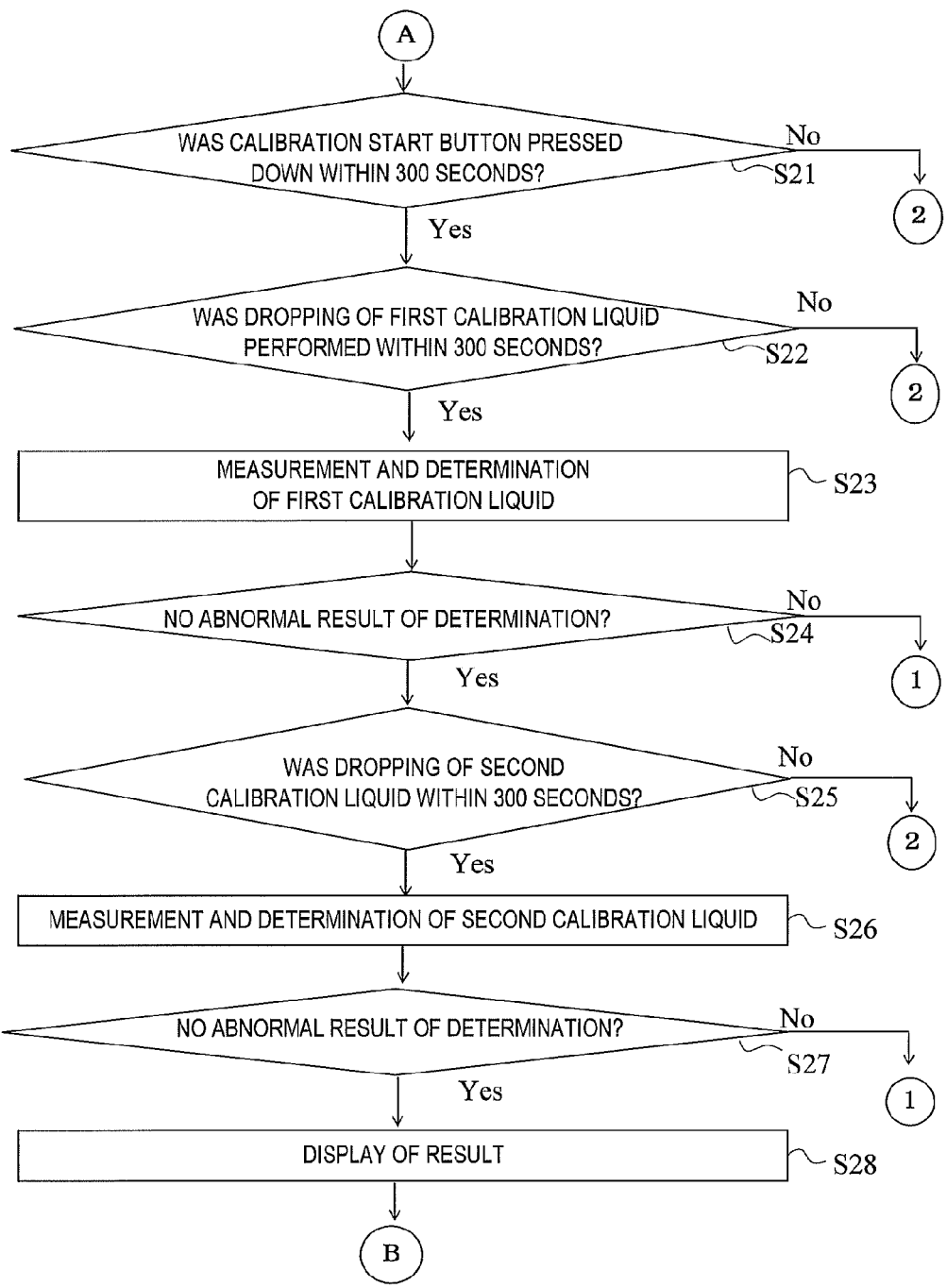
FIG. 3B is a flowchart illustrating a measuring method using the biochemical instrument illustrated in FIG. 1.
Figure 4:
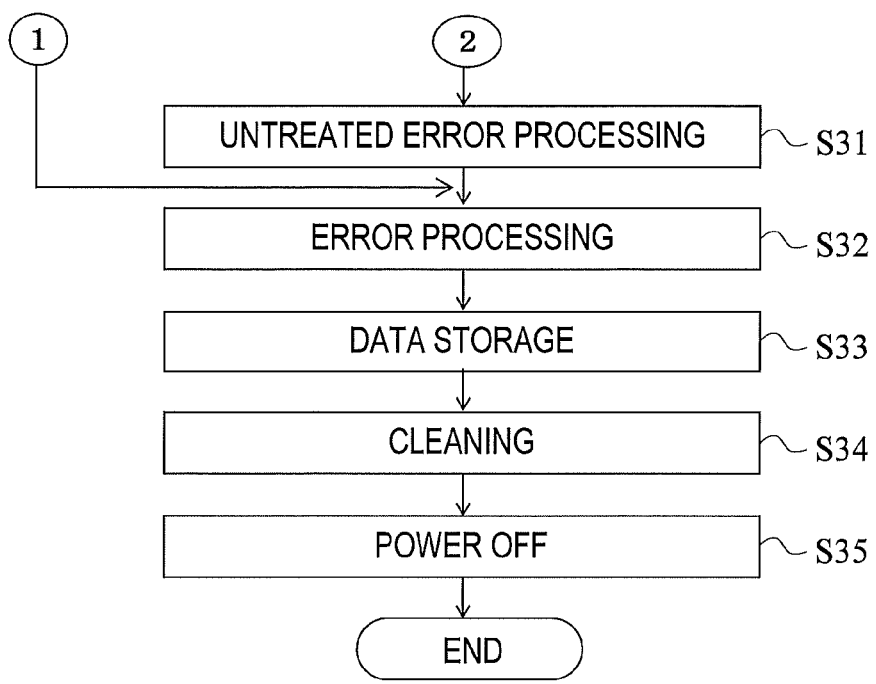
FIG. 4 is a flowchart illustrating an error processing in the measuring method using the biochemical instrument illustrated in FIG. 1.
Figure 5:
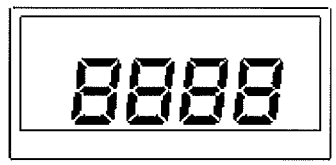
FIG. 5A to FIG. 5D are drawings illustrating items to be displayed on a display in a measuring mode.
Figure 5:
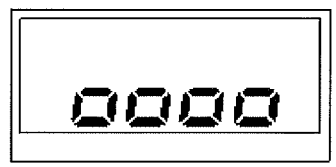
Figure 5:
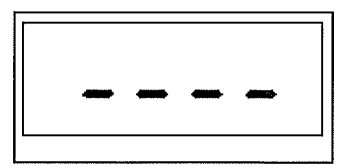
Figure 5:
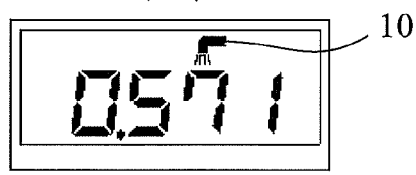
Figure 6:
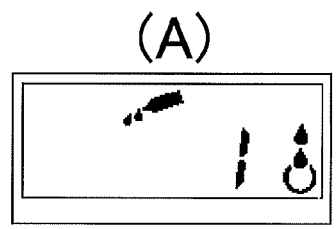
FIG. 6A to FIG. 6E are drawings illustrating items to be displayed on the display in a calibration mode.
Figure 6:
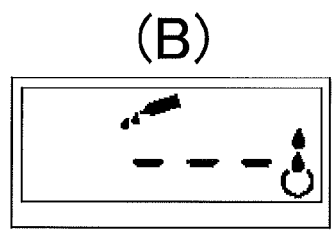
Figure 6:
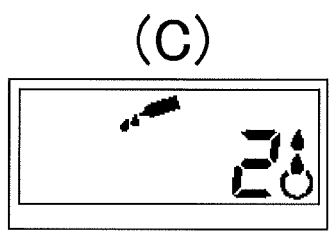
Figure 6:
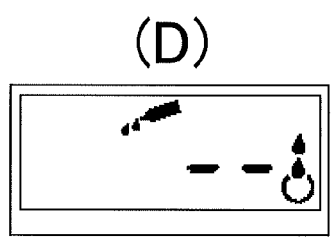
Figure 6:
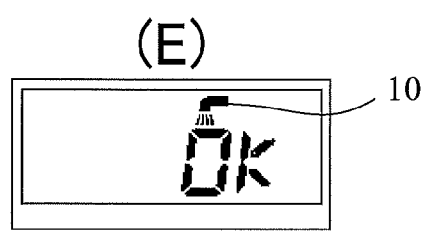

The method of measuring the sample liquid to be measured using the biochemical instrument 1 will be described with reference to flowcharts illustrated in FIG. 3A, FIG. 3B and FIG. 4, and FIG. 5, and FIG. 6. FIG. 3A and FIG. 3B are the flowcharts illustrating the measuring method using the biochemical instrument of the invention; FIG. 4 is the flowchart illustrating an error processing in the measuring method using the biochemical instrument; FIG. 5A to FIG. 5D are drawings illustrating items to be displayed on a display in a measuring mode; and FIG. 6A to FIG. 6E are drawings illustrating items to be displayed on the display in a calibration mode.

In order to start the measurement by the biochemical instrument 1 at first, the sensor holder 5 is rotated and expands via the hinge 19 as illustrated by the solid line in FIG. 1, a power source of the biochemical instrument 1 is turned ON by the hinge switch 19a and switched to the measurable state (Step S1).

Subsequently, the controller 17 confirms the remaining amount of battery of the power source 25 (Step S2). When the voltage of the battery is, for example, 2.5 V or higher (Yes in Step S2), it is determined that the remaining amount of the battery is sufficient, and the procedure goes to the next Step S4. When the voltage of the battery is less than 2.5 V (No in Step S2), an alarm such as illuminating a battery mark on the display 9 is issued to notify the user the fact that the remaining amount of battery is low (Step S3). The user replaces the battery with a new battery as needed. In the invention, a threshold value about the remaining amount of battery is not limited to 2.5V described above.

Subsequently, the controller 17 performs determination of the number of times of usage and the number of days of usage of the glucose sensor 11 stored in the storage 23. When the number of times of usage of the glucose sensor 11 is, for example, less than 200 times, or when the number of days of usage of the glucose sensor 11 is less than 60 days from the first day of use, for example, (Yes in Step S4), it is determined that the time does not reach the time for replacement of the glucose sensor 11 (still has reliable accuracy of measurement), and the procedure goes to the next Step S6. In the invention, the threshold value about the number of times of usage is not limited to 200 times as described above, and a threshold value about the above-described number of days is not limited to above-described 60 days. The change of threshold value may be performed at the point of factory production or at the time of replacement of the sensor with improved the performance of the biochemical instrument 1.

When the number of times of usage of the glucose sensor 11 is 200 times or more, or when the number of days of usage of the glucose sensor 11 is 60 days or more from the first day of use, (No in Step S4), an alarm encouraging the user to replace the glucose sensor 11 is displayed on the display 9 to let the user know that it is time to replace the glucose sensor 11 (Step S5). The user replaces the glucose sensor 11 by a new one as needed.

Subsequently, in a state in which the cap 7 is mounted, that is, in a state in which the glucose sensor 11 is immersed in (in contact with) the storage liquid 2, the pressure applying unit 13 applies a constant potential to a point between the working electrode 11a and the counter electrode 11b, and the current value of a current flowing from the working electrode 11a to the counter electrode 11b during the waiting state and acquired by the current detecting unit 15 is stored in the storage 23 as a base output value, and whether or not the base output value is within a range of a predetermined defined value is determined (Step S6, T1 illustrated in FIG. 7). In the example illustrated in FIG. 7, a base output value is assumed to be A1 [nA (nano ampere)]. When the base output value is within a normal range (Yes in Step S6), it is determined that the glucose sensor 11 and the storage liquid 2 are normal, and the procedure goes to the next Step S7. In contrast, when the base output value is not within the normal range (No in Step S6), it is determined that the glucose sensor 11 or the storage liquid 2 is abnormal, and the procedure goes to the error processing described later (illustrated in FIG. 4, Step S32), and the process is stopped.

Then, the peripheral temperature of the environment in which the biochemical instrument 1 is used is measured. When the temperature is between 0° C. to 40° C. inclusive, it is determined to be the normal temperature (Yes in Step S7). However, when the temperature is out of the above-described range, the glucose sensor 11 or the storage liquid 2 may get out of order due to the temperature, and hence the results of measurement from then onward may be affected thereby. Therefore, if it is determined that the temperature is not normal (No in Step S7), it is determined that the glucose sensor 11 or the storage liquid 2 is abnormal, and the procedure goes to the error processing described later (illustrated in FIG. 4, Step S32), and the process is stopped. It is also possible to add a function to measure the peripheral temperature of the biochemical instrument 1 when not in use (when being stored), store the measured temperature in the storage 23, and determine whether or not the temperature of the biochemical instrument 1 when not in use (when being stored) is normal in Step S7. In the invention, the threshold value about the temperature is not limited to the above-described range. The change of threshold value of the temperature may be performed at the point of factory production or at the time of replacement of the sensor with improved the performance of the biochemical instrument 1

Measuring Mode

When the determination in Step S7 is terminated, confirmation of an initial operation of the biochemical instrument is terminated, and the mode is converted into the measuring mode. The user may remove the cap 7 from the sensor holder 5 for use (T2 illustrated in FIG. 7). At this time, the display 9 displays a screen of the initial state as illustrated in FIG. 5A.

First of all, the controller 17 determines whether or not the battery is replaced in Step S3, and whether or not the glucose sensor 11 is replaced in Step S5. If there is no record of replacement stored in the storage 23 and it is determined that the replacement has not been performed (Yes in Step S8), the state of the glucose sensor 11 is considered not to be changed from the state at the time of the previous measurement, and the procedure goes to the next Step S9.

When the replacement of the battery or the replacement of the glucose sensor 11 is performed (No in Step S8), it is required to perform an initial setting (zero-point updating) of the glucose sensor 11. Therefore, the procedure goes to Step S21 in the calibration mode in order to force the execution of calibration, where the calibration of the glucose sensor 11 is performed.

Subsequently, the controller 17 determines how many times the measurement has been performed after the previous calibration from the time counter 21, and if it is 24 times or less (Yes in Step S9), it is within a guaranteed number of times that the accuracy of the glucose sensor 11 is maintained, so that the procedure goes to the next Step S10. If the number of times of measurement which has been performed more than 24 times (No in Step S9), since it is beyond the guaranteed number of times that the accuracy of the electrodes of the glucose sensor 11 is maintained, the accuracy of the result of measurement of the glucose sensor 11 in this state may vary. Therefore, the procedure goes to Step S21 in the calibration mode, where the calibration of the glucose sensor 11 is performed. Even when the number of times of measurement which has been performed more than 24 times, the execution of the calibration mode is a recommended execution for maintaining the accuracy of the electrodes of the glucose sensor 11, and hence the procedure may go to the next Step S10 without proceeding to the calibration mode. In the invention, the above-described threshold value about the number of times of measurement which has been performed is not limited to 24 times as described above. The change of threshold value may be performed at the point of factory production or at the time of replacement of the sensor with improved the performance of the biochemical instrument 1.

Subsequently, the controller 17 determines how many days have elapsed after the previous calibration from the time counter 21, and if it is 7 days or less, for example (Yes in Step S10), it is within a guaranteed number of days that the glucose sensor 11 can maintain the accuracy, so that the procedure goes to the next Step S11. In the invention, the threshold value about the number of days is not limited to seven described above. The change of threshold value may be performed at the point of factory production or at the time of replacement of the sensor with improved the performance of the biochemical instrument 1.

If move than seven days have been elapsed from the previous calibration (No in Step S10), since it is beyond the guaranteed number of days that the accuracy of the glucose sensor 11 is maintained, the accuracy of the result of measurement of the glucose sensor 11 in this state may vary. Therefore, the procedure goes to Step S21 in the calibration mode, where the calibration of the glucose sensor 11 is performed. Even when more than seven days have been elapsed from the previous calibration, the execution of the calibration mode is the recommended execution for maintaining the accuracy of the electrodes of the glucose sensor 11, and hence the procedure may go to the next Step S11 without proceeding to the calibration mode.

Subsequently, the controller 17 determines whether or not a variety of errors occurred in the process and the process is terminated by an untreated error processing (Step S31) or the error processing (Step S32) when the biochemical instrument 1 is used previously from the storage 23. If a variety of the errors did not occur (Yes in Step S11), the state of the glucose sensor 11 is still in the state when having terminated normally at the previous time, and hence the procedure goes to the next Step S12. At this time, the display 9 displays a screen of waiting for dropping of the sample liquid to be measured as illustrated in FIG. 5B.

If a variety of the errors occurred (No in Step S11), since a problem occurs in the state of the electrode of the glucose sensor 11, the accuracy of the result of measurement of the glucose sensor 11 in this state may vary. Therefore, the procedure goes to Step S21 in the calibration mode, where the calibration of the glucose sensor (biosensor) 11 is performed. Even when a variety of the errors occurred, the execution of the calibration mode is the recommended execution for maintaining the accuracy of the electrodes of the glucose sensor 11, and hence the procedure may go to the next Step S12 without proceeding to the calibration mode.

Subsequently, the sample liquid to be measured is dropped on the glucose sensor 11 via the opening 5a of the biochemical instrument 1. Subsequently, the user is required to drop the sample liquid to be measured within 300 seconds from the moment when the screen of waiting for dropping is displayed. If the dropping is performed within 300 seconds (Yes in Step S12), the procedure goes to the next Step S13. When 300 seconds have elapsed (No in Step S12), the glucose sensor 11 is dried, and hence the accuracy of the result of measurement may not be guaranteed, so that the procedure goes to the untreated error processing (Step S31).

When the sample liquid to be measured is dropped into contact with the glucose sensor 11, the measurement of the sample liquid to be measured is performed (Step S13). The current value of the output current flowing from the working electrode 11a to the counter electrode 11b is acquired across a predetermined period by the current detecting unit 15, and a maximum value P from among the acquired current values is stored in the storage 23 as a peak current value, and the controller 17 performs arithmetic operation of the results of measurement on the basis of the difference between the base output value acquired in Step S6 and the peak current value acquired in the Step S13 and displays the result of measurement on a result of measurement display screen on the display 9 as illustrated in FIG. 5D (Step S14). Also, a cleaning mark 10 which encourages the user to perform cleaning is displayed on the display 9. While performing the arithmetic operation of the result of measurement, an animation of a plurality of "–" signs as illustrated in FIG. 5C reduced gradually with the progress of the arithmetic operation may be displayed on the display 9 as an interpretation.

Data of the result of measurement is stored in the storage 23 (Step S15). Subsequently, the user cleans the glucose sensor 11 by using a predetermined detergent (Step S16). When the cleaning is performed, the cleaning mark 10 is extinguished and a display encouraging the user to store the glucose sensor 11 (not illustrated) blinks on and off.

Subsequently, the user is required to perform the cleaning within 300 seconds from the moment when the result of measurement display screen is displayed. If the cleaning is performed within 300 seconds (Yes in Step S16), the procedure goes to the next Step S17. When 300 seconds have elapsed (No in Step S16), the glucose sensor 11 is dried, and hence the accuracy of the result of measurement from the next time onward may not be guaranteed, so that the procedure goes to the untreated error processing (Step S31).

Subsequently, when turning the power source OFF, the glucose sensor 11 is covered with the cap 7 and is immersed in the storage liquid 2. Furthermore, when the user rotates and folds the sensor holder 5 via the hinge 19, the biochemical instrument 1 is brought into the waiting state by the hinge switch 19a. Simultaneously, at the timing when the sensor holder 5 is folded, the count of the elapsed time by the time counter 21 is started, and the measuring mode is terminated (Yes in Step S17). Also, a time to get stabilized according to sensor characteristics is required until the base output value returns back to the reference value. Needless to say, when the biochemical instrument 1 is kept in the waiting state, the time counter 21 is operated by a waiting power.

Calibration Mode

Subsequently, the calibration method of the biosensor of the invention will be described.

When it is determined to be No (that is, the calibration is required) in Steps S8 to S11, the mode is converted to the calibration mode in which the calibration of the glucose sensor 11 is performed. By pressing a calibration start button (not illustrated) down, the calibration mode is started (Step S21, T3 illustrated in FIG. 7).

A screen which encourages the user to drop the first calibration liquid onto the glucose sensor 11 as illustrated in FIG. 6A is displayed on the display 9. If the user drops the first calibration liquid onto the glucose sensor 11 into contact therewith within 300 seconds, for example, from a moment when the screen which encourages the dropping is displayed (Yes in Step S22, T2 illustrated in FIG. 7), an output value (first actual measured value) of the glucose sensor 11 when the first calibration liquid comes into contact with the glucose sensor 11 is acquired, and whether or not the value is within the predetermined range is determined (Step S23). Here, the predetermined range in the determination may be set according to a value of standard of the glucose sensor 11 as needed. When 300 seconds have elapsed before the first calibration liquid is dropped (No in Step S22), the glucose sensor 11 is dried, and hence the result of measurement may not be guaranteed, so that the procedure goes to the untreated error processing (Step S31).

A first output value is obtained by subtracting the base output value A1 from the first actual measured value. While acquiring and determining the first output value (T4 to T5 illustrated in FIG. 7), an animation of a plurality of "-" signs as illustrated in FIG. 6B reduced gradually with the progress of the arithmetic operation may be displayed as an interpretation. The time from T4 to T5 in the invention is assumed to be, for example, 6 to 30 seconds. In the example illustrated in FIG. 7, a current value as the first actual measured value is A2 [nA].

When there is no abnormality in determination of the first output value (Yes in Step S24), that is, when the first output value is within the predetermined range, the procedure goes to a second calibration liquid dropping process (Step S25). When there is an abnormality in result of calibration of the first calibration liquid (No in Step S24), that is, when the result of calibration is out of the predetermined range, the procedure goes to the error processing (Step S32).

Figure 7:
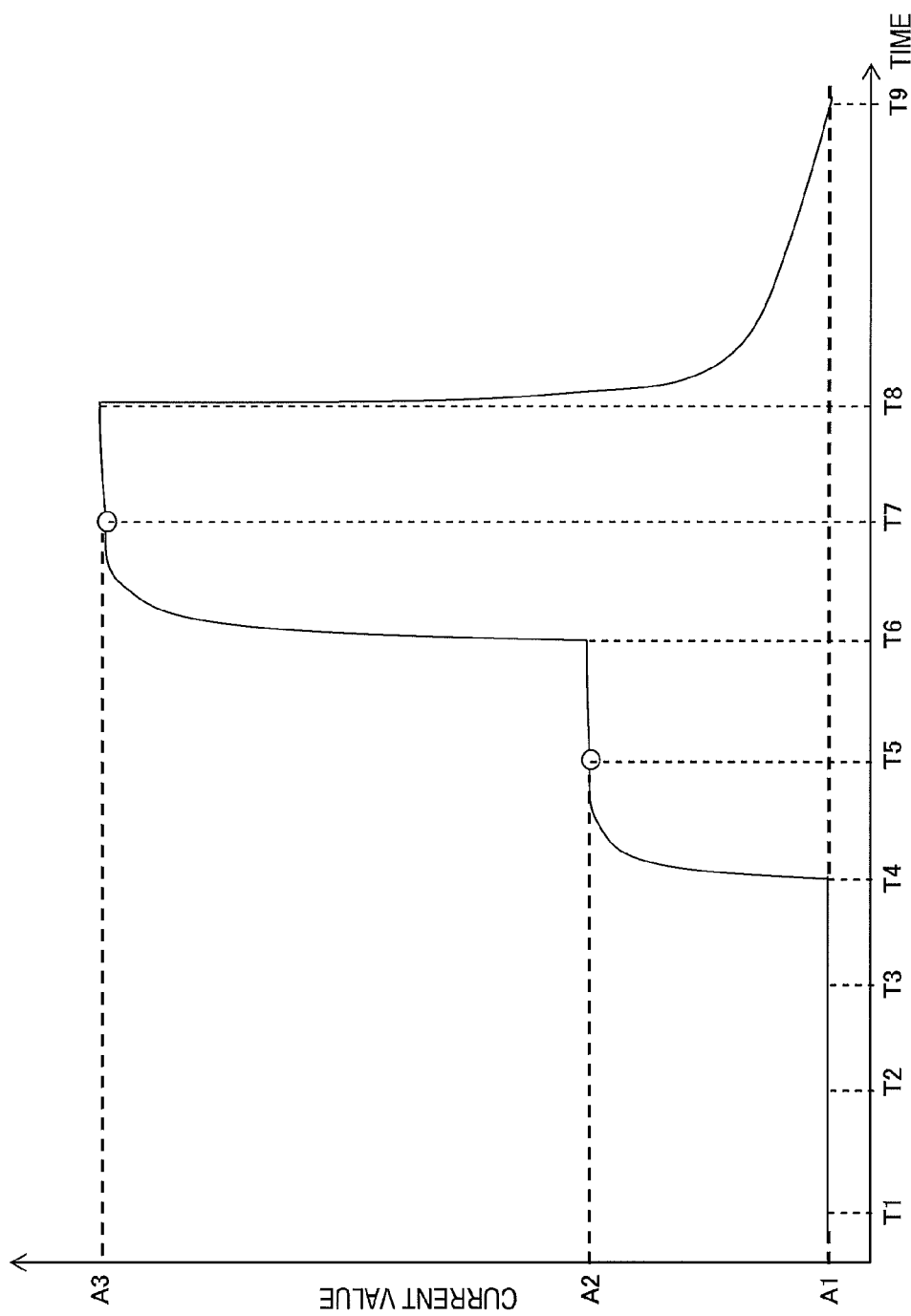
FIG. 7 is a graph schematically illustrating a change in current value (a sensor output value) at the time of calibration using the biochemical measuring device illustrated in FIG. 1.

The display 9 displays (notifies) a screen which encourages the user to drop the second calibration liquid onto the glucose sensor 11 as illustrated in FIG. 6C (illustrated in FIG. 7, T5 to T6). A buzzer sounds (notifies) together with this display. In this manner, when a first notifying step which encourages the user is included between the contact with the first calibration liquid and the contact with the second calibration liquid, described later, and the first notifying step is started between 6 seconds to 20 seconds after the contact with the first calibration liquid, the user is able to know the timing to bring the second calibration liquid into contact as soon as possible, and hence further reduction of the calibration working time is enabled, and the glucose sensor 11 may also be prevented from drying. If the user drops the second calibration liquid having a different concentration from that of the first calibration liquid onto the glucose sensor 11 into contact therewith within 300 seconds from a moment when the screen which encourages the dropping is displayed (Yes in Step S25, T6 in FIG. 7), an output value (second actual measured value) of the glucose sensor 11 when the second calibration liquid comes into contact with the glucose sensor 11 is acquired, and the time for replacement of the glucose sensor 11 is determined on the basis of the first output value and a second output value described later (Step S26). Here, the determination of the time for replacement may be achieved by determining whether or not the first output value and the second output value described later satisfy a predetermined relationship, and the detailed description will be given later. When 300 seconds have elapsed before the second calibration liquid is dropped (No in Step S25), the glucose sensor 11 is dried, and hence the result of measurement may not be guaranteed, so that the procedure goes to the untreated error processing (Step S31).

The second output value is obtained by subtracting the base output value A1 from the second actual measured value. While acquiring and determining the second output value (T6 to T7 illustrated in FIG. 7), an animation of a plurality of "–" signs as illustrated in FIG. 6D reduced gradually with the progress of the arithmetic operation may be displayed. The time from T6 to T7 in the invention is assumed to be, for example, 6 to 30 seconds. In the example illustrated in FIG. 7, a current value as the second actual measured value is A3 [nA].

When there is no abnormality in determination of the second output value (Yes in Step S27), that is, when the first output value and the second output value satisfy the predetermined relationship, it is determined that the glucose sensor 11 does not reach the time for replacement yet, and the procedure goes to the display of the result (Step S28, T7 illustrated in FIG. 7). When there is abnormality in determination of the second output value (No in Step S27), that is, when the first output value and the second output value do not satisfy the predetermined relationship, it is determined that the glucose sensor 11 reaches the time for replacement, and the procedure goes to the error processing (Step S32).

The display of the result (Step S28) displays the fact that the calibration mode is normally terminated as illustrated in FIG. 6E, and notifies the user that the glucose sensor 11 does not reach the time for replacement yet. The cleaning mark 10 configured to encourage the user to perform the cleaning is illuminated (notified). In this manner, when the second notifying step which encourages the user is included between the contact with the second calibration liquid and a step of cleaning the biosensor, and the second notifying step is started between 6 seconds to 20 seconds after the contact with the second calibration liquid, the user is able to know the timing to clean the biosensor, and hence further reduction of the calibration working time is enabled, and the glucose sensor 11 may also be prevented from drying. Subsequently the data of the result of measurement is stored in the storage 23 (Step S15), and then the user cleans the glucose sensor 11 with a predetermined detergent (Step S16, T8 illustrated in FIG. 7). The current value A3 drops to A1 by the cleaning (T9 illustrated in FIG. 7), but the time to get stabilized according to the sensor characteristics is required until the current value drops to A1 (T8 to T9 illustrated in FIG. 7).

Figure 8A:
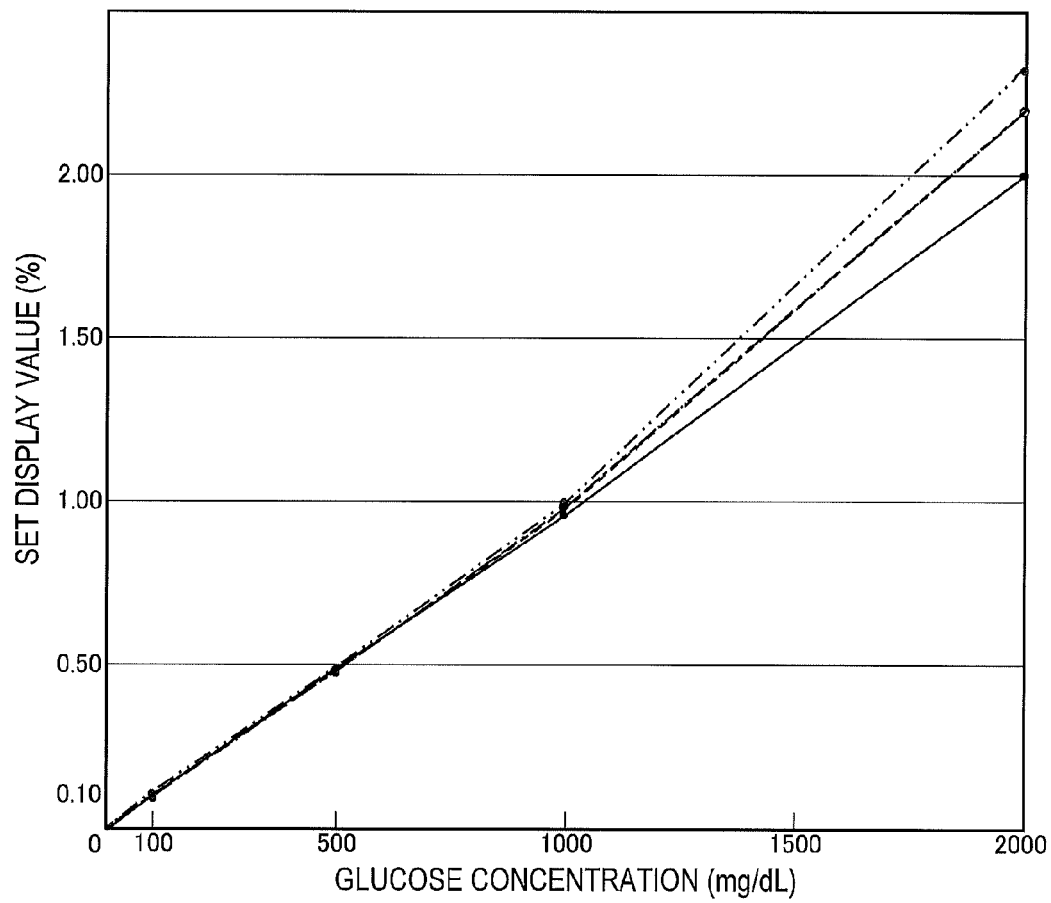
FIG. 8A is a drawing illustrating display values of a measuring sensor after having used a calibration method of the invention.
Figure 8B:
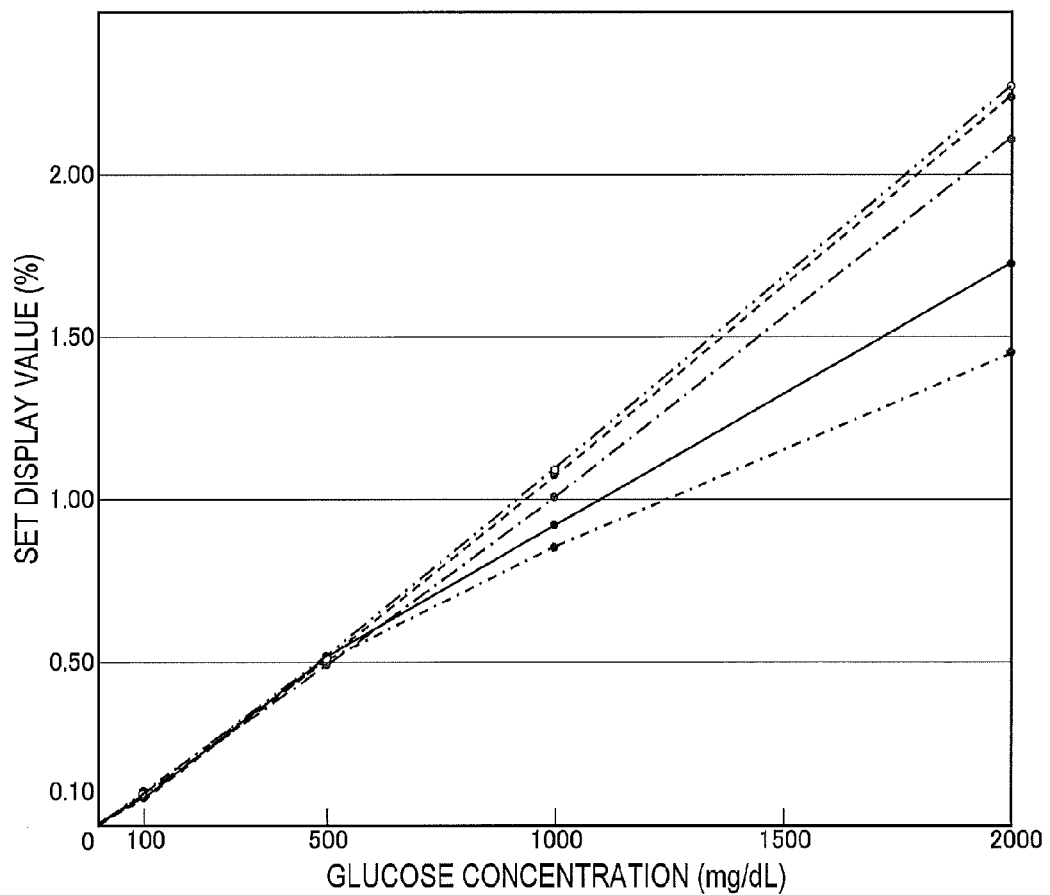
FIG. 8B is a drawing illustrating display values of the measuring sensor after having used a calibration method of the related art.

Here, the calibration method of the invention executed as the above-described calibration mode (Steps S21 to S28) will be described with reference to FIG. 7, FIG. 8, and FIG. 9 in further detail. FIG. 7 is a graph illustrating a change in current value at the time of calibration using the biochemical instrument according to the invention; FIG. 8A is a drawing illustrating display values of the measuring sensor after having used the calibration method of the invention, FIG. 8B is a drawing illustrating display values of the measuring sensor after having used a calibration method of the related art; and FIG. 9 is a flowchart illustrating a two-point calibration method of the related art.

Figure 9:
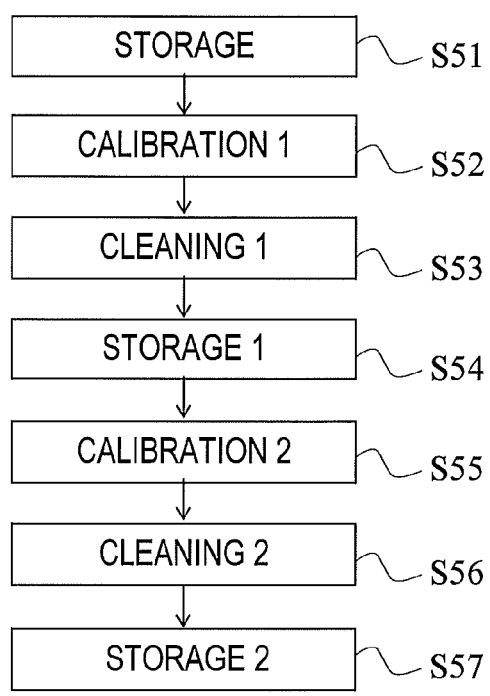
FIG. 9 is a flowchart illustrating a two-point calibration method of the related art.

The calibration method of the related art on the basis of a several-point calibration that is a method of performing the calibration a plurality of times continuously is performed according to the flow illustrated in FIG. 9. The glucose sensor immersed in the storage liquid in the stored state is taken out in Step S51, the first calibration liquid is dropped in a calibration 1 (Step S52), then a cleaning 1 for cleaning the first calibration liquid (Step S53) is performed, and stored 1 by being immersed in the storage liquid (Step S54), and the time to get stabilized according to the sensor characteristics is caused to go by until the glucose sensor is returned to the stabilized state, that is, until the base current value is returned to the stable state. Subsequently, after the second calibration has been dropped in a calibration 2 (Step S55), then a cleaning 2 (for cleaning the second calibration liquid Step S56) is performed and stored 2 by being immersed in the storage liquid (Step S57), and the glucose sensor is returned to the stabilized state.

In contrast, the calibration method of the invention includes bringing the first calibration liquid into contact with the biosensor in a first step (Step S21) as illustrated in FIG. 3A and FIG. 3B, bringing the second calibration liquid into contact continuously therewith without performing a cleaning operation of the first calibration liquid after a predetermined time has elapsed in a second step (Step S25), cleaning after a predetermined time has elapsed (Step S16), immersing and the storing the biosensor in the storage liquid, and returning the glucose sensor 11 into a stable state.

FIG. 7 is a graph schematically illustrating a change in current value (a sensor output value) at the time of calibration of the invention. A1[nA] indicates a base current value, and when the first calibration liquid is dropped into contact with the glucose sensor 11 at T4 (Step S21), the current value as an output value of the glucose sensor 11 is increased to A2 [nA] as chemical reaction. Subsequently, when the second calibration liquid is dropped into contact with the glucose sensor 11 at T6 (Step S25), the current value as an output value of the glucose sensor 11 is increased to A3 [nA]. Then, the glucose sensor 11 is cleaned at T8 (Step S16), and is immersed in the storage liquid for a certain period, so that the base current value A1 [nA] before the calibration is restored.

In the invention, in comparison with the related art, the processes of the cleaning (Step S53 in FIG. 9) and the storage (Step S54 in FIG. 9) may be omitted, the number of steps of the calibration operation may be reduced, and the entire working time required for the calibration may be reduced.

By using the calibration liquids having a different concentrations like the first calibration liquid and the second calibration liquid, which are the calibration liquid of the invention, the accuracy of the glucose sensor is improved than by the calibration method of the related art (in particular, one-point calibration). As a result on the basis of the study relating to the invention, as regards the concentrations of the first calibration liquid and the second calibration liquid, when the concentration of the first calibration liquid to be higher than that of the second calibration liquid, useless impurities was generated. However, when the concentration of the second calibration liquid was set to be higher than that of the first calibration liquid, generation of the impurities was reduced in comparison with the case where the concentration of the first calibration liquid was set to be higher than that of the second calibration liquid, and hence the accuracy of the glucose sensor after the calibration was improved. Therefore, the calibration method is preferably performed by increasing the concentration of the second calibration liquid than that of the first calibration liquid.

The concentration ratio between the first calibration liquid and the second calibration liquid used in the glucose sensor 11 according to this embodiment is preferably set to "first calibration liquid:second calibration liquid=1:2 to 6", and more preferably, "1:4" and, for example, the concentration of the first calibration liquid is set to 250 mg/dL and that of the second calibration liquid is set to 1000 mg/dL.

Here, the determination of the time for replacement (Step S27) may be performed by determining whether or not the first output value and the second output value satisfy the predetermined relationship. As an example, in the case of the concentration ratio of "first calibration liquid:second calibration liquid=1:4", as the ratio between the value obtained by subtracting the base output value A1 from the current value A2 generated by dropping the first calibration liquid (the first output value) and the value obtained by subtracting the base output value A1 from the current value A3 generated by dropping the second calibration liquid (the second output value), a normal range of the second output value may be set to a value within −35% to +5%, which is four times the first output value, that is;

$$((A2-A1)\times 4)\times(1-0.35) \leq A3-A1 \leq ((A2-A1)\times 4)\times(1+0.05).$$

In other words, in the invention, the determination of the time for replacement (the second step) corresponds to the determination of whether or not the first output value and the second output value satisfy the relationship;

$$(\text{first output value} \times n)\times(1-0.35) \leq \text{second output value} \leq (\text{first output value} \times n)\times(1+0.05)$$

(where, $n$=concentration of the second calibration liquid/concentration of the first calibration liquid).

In terms of the characteristics of the glucose sensor, the value of the high-concentration measurement does not make errors in the plus direction in many cases, and if the difference in output values with the calibration liquids having four times difference in concentration is approximately 2.5 times or less, normal measurement is not achieved due to the deterioration of the glucose sensor (such as deactivation of enzymes), so that the range as described above is preferable.

FIG. 8A is a graph illustrating individual differences of the display values of five of the biosensors after the calibration on the basis of the calibration method of the invention, and FIG. 8B is a graph illustrating individual differences of the display values of the five biosensors after the calibration with one sort of liquid of the related art.

In FIG. 8A of the invention, variations in measured values (current values) of five of the glucose sensors are approximately 8% in a concentration of the sample liquid to be measured of 100 mg/dL, approximately 1.1% in 500 mg/dL, approximately 0.9% in 1000 mg/dL, and approximately 5.5% in 2000 mg/dL. However, in FIG. 8B of the related art, the variations in measured values (current values) measured by the five glucose sensors are increased with increase of the concentrations of the sample liquid to be measured such as approximately 9% in 100 mg/dL, approximately 1.2% in 500 mg/dL, approximately 10.8% in 1000 mg/dL, and approximately 18.1% in 2000 mg/dL. From these results, it is understood that the calibration method of the glucose sensor of the invention is capable of calibrating the glucose sensor with high degree of accuracy while achieving the reduction of the number of operation steps and the working time required for the user in comparison with the calibration method of the biosensor of the related art.

Error Mode

Subsequently, the flow of the error mode in a case where the error occurs during the processing will be described with reference to FIG. 4.

The untreated error processing (Step S31) is an error processing executed when a variety of errors occur and the user does not perform a predetermined operation (Step S12, Step S21, Step S22, and Step S25) within the predetermined period (for example, within 300 seconds). The untreated error processing is executed because if the predetermined operation is not performed within the predetermined time, the glucose sensor 11 is dried, and if the power is distributed to the glucose sensor 11 in the dried state, the glucose sensor 11 may be destroyed. The contents of the untreated error processing include, for example, issuing an alarm (notifying) the user by causing the buzzer to sound at five seconds intervals from after 30 seconds described above, and if the user still does not perform the operation, the controller 17 issues an instruction to stop application of the voltage to the voltage application portion 13 after 300 seconds. Then, the display 9 is extinguished. When the pressing down of the operating unit 6 or the state in which the hinge switch 19a is folded is sensed, the procedure goes to the error processing (Step S32).

The error processing (Step S32) causes the display 9 to display an error number by illumination. At this time, a configuration in which the user is encouraged to execute the cleaning and/or execute the calibration by displaying the cleaning mark 10 and/or a display encouraging the calibration blinked ON and OFF.

As described above, when there is abnormality in determination of the second output value (No in Step S27), that is, when the first output value and the second output value do not satisfy the predetermined relationship, a display indicating that the glucose sensor 11 reaches the time for replacement as the error processing (Step S32) to notify the same to the user and encourage the user to perform the replacement of the glucose sensor 11.

Subsequently, the controller 17 records the data including the state in which the error occurred in the storage 23 (Step S33). It is for converting the mode to the calibration mode by the determination in Step S11 if there is a record of occurrence of the error when the power source is turned ON for the next time.

Subsequently, the user cleans the glucose sensor 11 by using a predetermined detergent (Step S34). When the cleaning is performed, the cleaning mark 10 is extinguished and a display encourages the user to store the glucose sensor 11 blinks ON and OFF instead.

Subsequently, the user puts the cap 7 on the glucose sensor 11 and immerses the same in the storage liquid 2. Furthermore, when the user rotates and folds the sensor holder 5, the power source is turned OFF by the hinge switch 19a (Step S35), the 1 is brought into the waiting state, and the error processing is terminated.

As described above, according to the embodiment described above, by performing the first calibration using the first calibration liquid and then performing the second calibration using the second calibration liquid having a predetermined different concentration, the second calibration is enabled without performing the cleaning operation of the first calibration liquid, so that reduction of the number of the operation steps and the working time required for the user is achieved.

By the employment of the calibration liquids having a different concentrations as the first calibration liquid and the second calibration liquid, variations in measurement errors of the measuring sensor by machine type after the calibration may be reduced in comparison with the calibration method on the basis of the one-point calibration of the related art, so that the result of measurement with high precision with small measurement errors by machine type may be obtained in the measurement of the sample liquid to be measured.

In addition, according to the embodiment described above, since the calibration is performed by determining whether or not the user has dropped the first calibration liquid on the glucose sensor 11, whether or not the user has dropped the second calibration liquid thereon, whether or not the user has performed the cleaning operation by the biochemical instrument 1, and displaying the required guidance on the display 9. Therefore, the user only has to perform the calibration operation according to the guidance, the button operation during the calibration operation is not necessary, so that the improvement of usability is achieved.

In this embodiment, although the sensor which employs glucose oxidase as enzyme and is configured to detect glucose is used, the invention is not limited thereto. For example, a sensor which uses lactate oxidase, alcohol oxidase, cholesterol oxidase, pyruvate oxidase, amino acid oxidase, ascorbic acid oxidase, or the like may be employed in order to detect the concentration of an organic substance such as lactic acid, alcohol, cholesterol, pyruvic acid, amino acid, ascorbic acid, and the like.

In the embodiment described above, the calibration method in which contact with the calibration liquid in the calibration mode is two times (the first calibration liquid and the second calibration liquid) has been described. However, the invention is not limited specifically thereto, and the calibration may be achieved by bringing third and fourth calibration liquids having different concentrations into contact.

In the embodiment described above, the example having the process of acquiring the output value (the first actual measured value) of the glucose sensor 11 when the first calibration liquid comes into contact with the glucose sensor 11 and determining whether or not the output value is within the predetermined range (Step S23) has been described. However, the invention is not limited specifically thereto and does not necessarily have to have this step.

The invention may be embodied in various modes without departing the essential characteristics. Therefore, needless to say, the embodiment described above is given only for description and does not limit the invention.

What is claimed is:

1. A biosensor calibration method, wherein a biosensor is configured to measure a concentration of a specific substance contained in sample liquid to be measured, the method comprising:

(a) measuring a base output value in a state in which the biosensor is covered with a cap and the biosensor is in contact with a storage liquid that is filled in an interior of the cap;

(b) acquiring a first output value that is output by the biosensor when first calibration liquid is brought into contact with the biosensor in a state in which the cap is removed from the biosensor, the first output value being obtained by subtracting the base output value from an actual measured value output by the biosensor;

(c) acquiring a second output value that is output by the biosensor when second calibration liquid having a different concentration of the specific substance from that of the first calibration liquid is brought into contact with the biosensor after the step (b) without performing a cleaning operation, the second output value being obtained by subtracting the base output value from an actual measured value output by the biosensor; and (d) determining whether or not the time for replacement of the biosensor has been reached on the basis of whether or not the first output value and the second output value satisfy a predetermined relationship based on a concentration ratio of the first calibration liquid and the second calibration liquid.

2. The biosensor calibration method according to claim 1, wherein the concentration of the second calibration liquid is higher than the concentration of the first calibration liquid.

3. The biosensor calibration method according to claim 1, wherein the second calibration liquid has a concentration twice to six times that of the first calibration liquid.

4. The biosensor calibration method according to claim 1, wherein the predetermined relationship is defined by $$(\text{first output value} \times n) \times (1-0.35) \leq \text{second output value} \leq (\text{first output value} \times n) \times (1+0.05)$$

(where, n=concentration of the second calibration liquid/concentration of the first calibration liquid).

5. The biosensor calibration method according to claim 1, further comprising a step of cleaning the biosensor after the step (c).

6. The biosensor calibration method according to claim 1, further comprising a first notifying step of encouraging a user to bring the second calibration liquid into contact with the biosensor from 6 seconds to 20 seconds after the contact of the first calibration liquid.

7. The biosensor calibration method according to claim 6, further comprising a second notifying step of encouraging the user to clean the biosensor from 6 seconds to 20 seconds after the contact of the second calibration liquid.

8. The biosensor calibration method according to claim 1, wherein the step (a) comprises determining whether or not the base output value is within a range of a predetermined defined value.

9. The biosensor calibration method according to claim 1, wherein the step (b) comprises determining whether or not the first output value is within a predetermined range.

10. The biosensor calibration method according to claim 1, wherein the step (a) comprising immersing the biosensor in the storage liquid that does not contain the specific substance.

11. The biosensor calibration method according to claim 1, further comprising:

(e) executing an untreated error processing to prevent the biosensor from being destroyed if a predetermined operation is not performed within a predetermined time; and (f) executing an error processing to encourage a user to execute cleaning and/or calibration of the biosensor.

12. A biochemical instrument comprising:

a biosensor configured to measure a concentration of a specific substance contained in sample liquid to be measured;

a cap; and a controller configured to perform the steps of:

(a) measuring a base output value in a state in which the biosensor is covered with the cap and the biosensor is in contact with a storage liquid that is filled in an interior of the cap;

(b) acquiring a first output value that is output by the biosensor when first calibration liquid is brought into contact with the biosensor in a state in which the cap is removed from the biosensor, the first output value being obtained by subtracting the base output value from an actual measured value output by the biosensor;

(c) acquiring a second output value that is output by the biosensor when second calibration liquid having a different concentration of the specific substance from that of the first calibration liquid is brought into contact with the biosensor after the step (b) without performing a cleaning operation, the second output value being obtained by subtracting the base output value from an actual measured value output by the biosensor; and (d) determining whether or not the time for replacement of the biosensor has been reached on the basis of whether or not the first output value and the second output value satisfy a predetermined relationship based on a concentration ratio of the first calibration liquid and the second calibration liquid.

13. A biochemical instrument comprising:

a biosensor configured to measure a concentration of a specific substance contained in sample liquid to be measured; and a controller configured to perform the steps of:

(a) acquiring a first output value that is output by the biosensor when first calibration liquid is brought into contact with the biosensor;

(b) acquiring a second output value that is output by the biosensor when second calibration liquid having a different concentration of the specific substance from that of the first calibration liquid is brought into contact with the biosensor after the step (a) without performing a cleaning operation; and (c) determining whether or not the time for replacement of the biosensor has been reached on the basis of whether or not the first output value and the second output value satisfy the relationship of:

$$(\text{first output value} \times n) \times (1-0.35) \leq \text{second output value} \leq (\text{first output value} \times n) \times (1+0.05)$$

(where, n=concentration of the second calibration liquid/concentration of the first calibration liquid).

* * * * *